United States Patent [19]

Dent

[11] Patent Number: 4,507,118
[45] Date of Patent: Mar. 26, 1985

[54] FITMENTS FOR INJECTION DEVICES

[75] Inventor: Hugh R. Dent, Stroud, England

[73] Assignee: Sterimatic Holdings Limited, Tortola, British Virgin Isls.

[21] Appl. No.: 510,752

[22] Filed: Jul. 1, 1983

[51] Int. Cl.³ ............................................. A61M 5/00
[52] U.S. Cl. ..................................... 604/198; 604/263
[58] Field of Search ................. 604/198, 197, 199, 263

[56] References Cited

U.S. PATENT DOCUMENTS

| 1,921,034 | 8/1933 | LaMarche | 604/197 |
| 2,888,924 | 6/1959 | Dunmire | 604/199 |
| 3,134,380 | 5/1964 | Armao | 604/198 |
| 3,354,881 | 11/1967 | Bloch | 604/199 |

Primary Examiner—John D. Yasko
Attorney, Agent, or Firm—Young & Thompson

[57] ABSTRACT

In order to minimize the risk of infection when a large number of animals are injected with the same needle, the injecting gun is provided with a stainless steel sleeve which surrounds the needle. The sleeve comprises a first tube attached to the needle connecting body and a second tube telescopically slidable within the first tube against a spring. A detachable plastics cap incorporating a sterilizing substance is fitted on the free end of the second tube. In use of the gun to inject an animal, the cap is applied to the proposed site of injection and pressure is applied to the gun to cause the tubes to telescope, so that the point of the needle passes through the sterilizing substance and punctures the skin of the animal. On releasing the applied pressure, the point of the needle will be withdrawn from the animal and will pass back through the sterilizing substance under the action of the spring.

12 Claims, 2 Drawing Figures

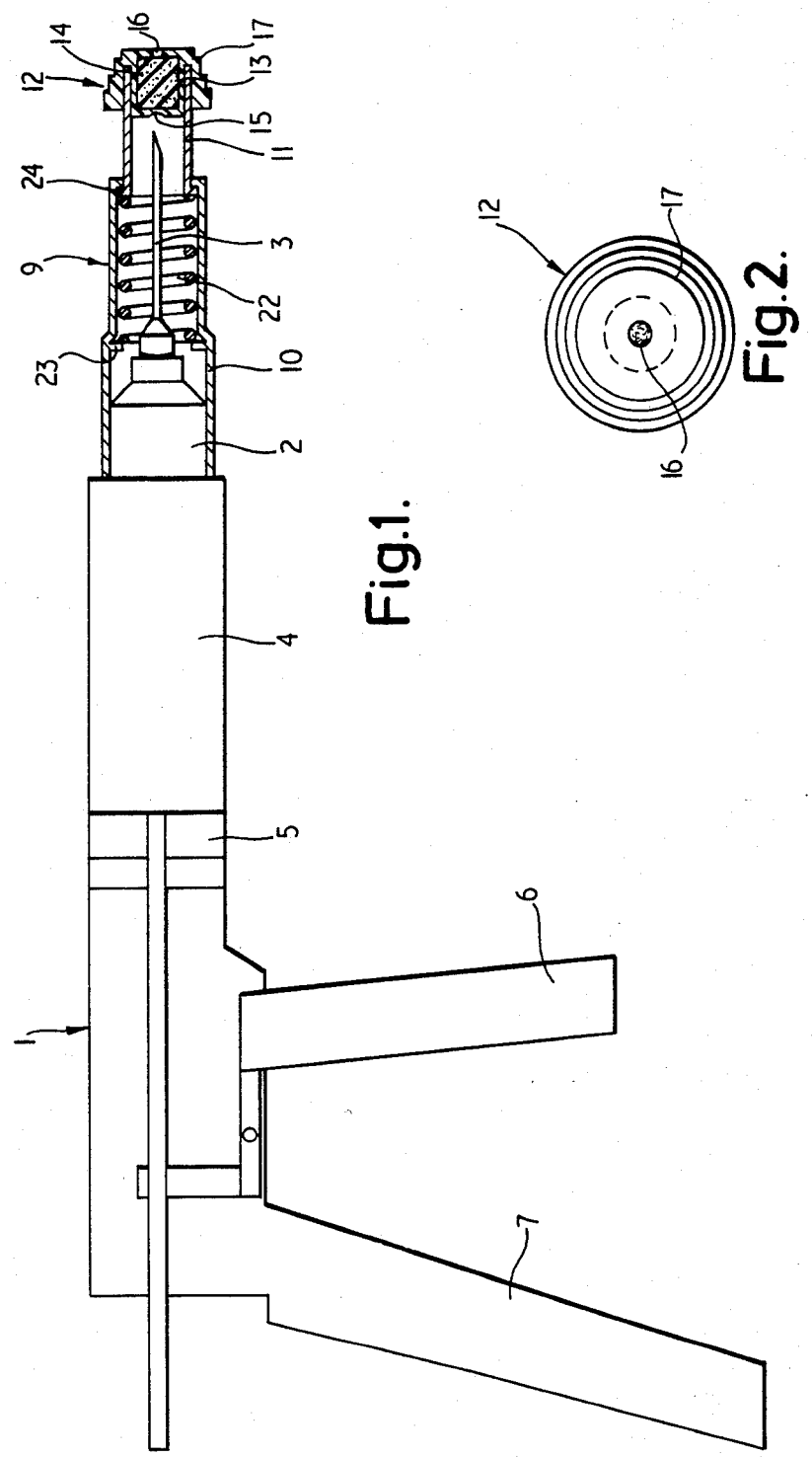

4,507,118

FITMENTS FOR INJECTION DEVICES

BACKGROUND OF THE INVENTION

This invention relates to fitments for injection devices of the kind in which injection liquid is delivered through a hollow needle. Such devices are used for injecting humans, animals, trees, fruit or vegetables, for example.

Farmers have for many years given routine oral drenches of anthelminthics to suppress the effects of intestinal and other parasitic worms in cattle, sheep and pigs. However these drenches only become effective after a relatively long period. Although it has recently become possible to achieve the same effect in a much shorter space of time by injecting the animal, there has been a reluctance by farmers to use the new method. This is because it is not usual to sterilize the site of injection either before or after injection. Moreover the same needle is often used for injecting a large number of animals without sterilizing the needle between each injection, in view of the large number of animals which have to be injected at one time, so that the site of injection often becomes infected leading to an abscess. Also, especially with sheep, there are several routine injections given to stop various clostridial complications, and each time the animal is injected it increases the risk of rejection of the carcass for human consumption due to abscesses. It is an object of this invention to provide injection devices of the kind referred to with fitments which enable the devices to be used by farmers to inject a large number of animals in a short space of time whilst minimising any subsequent infection at the site of injection.

SUMMARY OF THE INVENTION

According to the invention there is provided a sterilising fitment for an injection device of the kind in which injection liquid is delivered through a hollow needle, the fitment being provided to sterilise the needle prior to its application to the site of injection and again on withdrawal of the needle from the site of injection, which fitment comprises a collapsible sleeve for surrounding the needle, means at one end of the sleeve for attaching the sleeve to a needle support of the injection device, and a sterilising substance holder releasably carried by the other end of the sleeve to close off said other end so as to enclose the needle, the holder comprising an enclosure containing sterilising means, and the two ends of the collapsible sleeve being reciprocable relative to one another in the direction of the length of the needle and being resiliently biased in the extended position, whereby, in use, when an injection is effected by placing said other end of the sleeve against the injection site and applying pressure to the injection device in a direction towards the injection site, the point of the needle moves through the sterilising means within the enclosure into the injection site as the sleeve collapses under the applied pressure and subsequently moves back into the sleeve through the sterilising means as the sleeve reassumes its extended position on release of said pressure, and the holder may subsequently be replaced on said other end of the sleeve by a holder containing fresh sterilising means.

Whilst the word "sterilising" is used in this specification in the sense of killing micro-organisms, such as bacteria or viruses, it should be understood that it is not essential that all micro-organisms are killed, that is to say that the needle is rendered absolutely sterile. The sterilising means may, for example, comprise a sterilising substance in the form of a liquid, gel or powder.

Since the needle is sterilised before it punctures the skin, there is little chance of the wound being infected by the needle, even if the same needle is used for performing a number of injections. Furthermore, where the sterilising means comprise a sterilising substance, some of the sterilising substance coating the needle may be transferred to the site of the injection.

The sterilising means may comprise a body of absorbent material impregnated with a sterilising substance.

In one form of the invention the sterilising means comprise a radioactive substance so disposed as to provide within the fitment a radioactive sterilising field through which, when the fitment is attached to an injection device, at least a leading portion of the needle is movable prior to application of the needle to the site of injection.

In another form of the invention the sterilising means comprise a reservoir for a sterilising fluid in communication with a nozzle for injecting the fluid into a chamber which, when the fitment is attached to an injection device, surrounds at least a leading portion of the needle whereby said portion of the needle may be coated with said fluid prior to application of the needle to the site of injection.

The invention also provides an injection device comprising a support for a hollow needle, a reservoir for injection liquid, means for delivering injection liquid from the reservoir through the needle, and a fitment including means for sterilizing the needle prior to application of the needle to the site of injection.

BRIEF DESCRIPTION OF THE DRAWINGS

In order that the invention may be more fully understood, an embodiment of the invention will now be described, by way of example, with reference to the accompanying drawing, in which:

FIG. 1 is a schematic diagram of an injection device incorporating a fitment which is shown in section; and FIG. 2 is an end view of the fitment.

DETAILED DESCRIPTION OF THE DRAWINGS

The illustrated device comprises an injecting gun 1 of the type used for injecting cattle, sheep or pigs. The gun 1 includes a needle connecting body 2, a hollow metal needle 3, a reservoir 4 for injection liquid, a piston 5, an actuating lever 6 for displacing the piston 5 to supply injection liquid to the needle 3, and a handle 7. A stainless steel sleeve 9 is a push fit on the needle connecting body 2, a slot (not shown) optionally being provided in the end of the sleeve 9 to enable the end of the sleeve to expand slightly to accommodate the connecting body 2.

The sleeve 9 comprises a first tube 10 attached to the needle connecting body 2, and a second tube 11 telescopically slidable within the first tube 10. The second tube 11 is biased into its extended position by a return spring 22 within the first tube 10 between an annular flange 23 on the first tube 10 and an annular flange 24 on the second tube 11.

A detachable plastics cap 12 incorporating an enclosure 13 for a sterilizing substance is an interference fit on the free end of the second tube 11. The enclosure 13 contains a sponge 14 impregnated with a sterilizing gel. Furthermore the enclosure 13 incorporates a weakened portion 15 and an aperture 16 lying on the longitudinal axis of the needle 3. The cap 12 is provided with step formations 17 on its outer surface in order to make it easier to remove the cap 12 from the end of the second tube 11. If desired, a reservoir for sterilizing substance 5 may be clipped to the top of the gun 1, and sterilizing substance may be supplied to the cap 12 from this reservoir by means of a feed tube.

In use of the gun 1 to inject an animal, it is first ensured that the cylinder 4 contains a quantity of injection liquid and that a sterilizing cap 12 is fitted to the free end of the second tube 11. The end of the cap 12 is then applied to the proposed site of injection on the animal, and pressure is applied to the gun so as to cause the tubes 10, 11 to telescope so that the point of the needle 3 passes through the enclosure 13 and punctures the skin of the animal. More particularly the point of the needle 3 punctures the weakened portion 15 of the enclosure 13, moves through the impregnated sponge 14 and then passes through the aperture 16 in the end wall of the enclosure 13. The needle 3 is thereby cleaned and coated with a layer of the sterilizing gel prior to its penetrating the skin. The action of the needle puncturing the skin may serve to transfer sterilizing substance to the skin thereby sterilizing the site of the injection. When the needle 3 has been pushed through the skin to the required depth the lever 6 is operated to administer the required dose of injection liquid. Optionally the second tube 11 is guided within the first tube 10 by guides (not shown) which are slightly skew with respect to the longitudinal axis of the first tube 10 so that the tube 11 rotates through a small angle as the tubes are telescoped, thereby providing a scrubbing action on the needle 3 by the sponge 14.

As the needle 3 is withdrawn, the second tube 11 is caused to return to its extended position by the return spring 22 so that the point of the needle 3 passes back through the sponge 14, thereby again cleaning the needle 3 and coating it with a layer of sterilizing gel. The injection has then been completed and the gun 1 may be moved away from the skin of the animal. The gun 1 can then be used for performing a second injection without any further adjustment having to be made. A large number of injections may be made using the same needle 3 and the same sterilizing cap 12 without appreciably increasing the risk of infection.

In a modification of the above-described embodiment of the invention, the arrangement is such that the position of the enclosure 13 is adjusted relative to the needle 3 between each injection so that, on performing a second injection, the point of the needle 3 will pass through a different region of the sponge 14 to that through which it passed on performing the first injection. For example, the arrangement may be such that the enclosure 13 is rotatable and the point of the needle passes through the enclosure 13 along a path parallel to, but offset from, the axis of rotation of the enclosure 13. After the first injection has been carried out, the enclosure 13 may be rotated about its axis through a limited angle prior to the second injection being performed, this rotation possibly being performed by indexing means coupling the second tube 11 to the first tube 10 and actuated by telescoping of the tubes.

Instead of providing a sponge 14 impregnated with sterilizing substance through which the point of the needle 3 passes in use, a spray nozzle may be provided in a wall of the sleeve 9 for spraying the needle with a sterilizing liquid or powder when a valve is actuated by telescoping of the tubes 10 and 11. As a further alternative a sterilizing cap may be provided containing a radioactive substance which provides a radioactive sterilizing field through which the point of the needle 3 moves prior to an injection. The radioactive substance may be in the form of a radioactive coating on the internal walls of the cap, and screening is provided by means of lead.

In the embodiment illustrated the sleeve 9 is detachable from the gun 1 to enable a new needle 3 to be fitted to the gun 1. However it is also possible for the sleeve to be integrally formed with the remainder of the injection device, more particularly where the injection device is a disposable plastics syringe of the type used for injecting humans. In this case the sterilizing substance may be impregnated in a sponge provided at the end of a collapsible plastics sleeve surrounding the needle and comprising a flexible intermediate portion provided with slots extending substantially parallel to the axis thereof. On performing an injection, the flexible intermediate portion will bow outwardly enabling the point of the needle to move through the sponge prior to puncturing the skin.

I claim:

1. A sterilising fitment for an injection device of the kind in which injection liquid is delivered through a hollow needle, the fitment being provided to sterilise the needle prior to its application to the site of injection and again on withdrawal of the needle from the site of injection, which fitment comprises a collapsible sleeve for surrounding the needle, means at one end of the sleeve for attaching the sleeve to a needle support of the injection device, and a sterilising substance holder releasably carried by the other end of the sleeve to close off said other end so as to enclose the needle, the holder comprising an enclosure containing sterilising means, and the two ends of the collapsible sleeve being reciprocable relative to one another in the direction of the length of the needle and being resiliently biased in the extended position, whereby, in use, when an injection is effected by placing said other end of the sleeve against the injection site and applying pressure to the injection device in a direction towards the injection site, the point of the needle moves through the sterilising means within the enclosure into the injection site as the sleeve collapses under the applied pressure and subsequently moves back into the sleeve through the sterilising means as the sleeve reassumes its extended position on release of said pressure, and the holder may subsequently be replaced on said other end of the sleeve by a holder containing fresh sterilising means.

2. A fitment according to claim 1, wherein the sterilising substance holder is an interference fit on said other end of the sleeve.

3. A fitment according to claim 1, wherein said other end of the sleeve is received within an annular recess in the sterilising substance holder.

4. A fitment according to claim 1, wherein the sterilising means comprise a body of absorbent material impregnated with a sterilising substance.

5. A fitment according to claim 1, wherein the sterilising substance holder is disposed adjacent but beyond the pointed end of the needle when the fitment is attached to the injection device, whereby the needle enters and moves through the sterilising means upon said collapse of the sleeve.

6. A fitment according to claim 1, wherein the sterilising substance holder incorporates a weakened portion which may be pierced by the needle.

7. A fitment according to claim 1, wherein the collapsible sleeve comprises two telescoping tubes, one of which incorporates at one end said means for attaching the sleeve to the needle support of the injection device, and the other of which releasably carries the sterilising substance holder.

8. A fitment according to claim 1, wherein the collapsible sleeve comprises a flexible intermediate portion connecting the two ends of the sleeve.

9. A fitment according to claim 8, wherein the flexible intermediate portion comprises a plurality of circumferentially disposed longitudinal strips connecting said two ends, which strips bow outwardly as the two ends are moved towards one another.

10. An injection device comprising a support for a hollow needle, a reservoir for injection liquid, means for delivering injection liquid from the reservoir through the needle, and a fitment for sterilising the needle prior to application of the needle to the site of injection and again on withdrawal of the needle from the site of injection, the fitment comprising a collapsible sleeve for surrounding the needle, one end of the sleeve being attached to the needle support, and a sterilising substance holder releasably carried by the other end of the sleeve to close off said other end so as to enclose the needle, the holder comprising an enclosure containing sterilising means, and the two ends of the collapsible sleeve being reciprocal relative to one another in the direction of the length of the needle and being resiliently biased in the extended position, whereby, when an injection is effected by placing said other end of the sleeve against the injection site and applying pressure to the injection device in a direction towards the injection site, the point of the needle moves through the sterilising means into the injection site as the sleeve collapses under the applied pressure and subsequently moves back into the sleeve through the sterilising means as the sleeve reassumes its extended position on release of said pressure, and the holder may subsequently be replaced on said other end of the sleeve by a holder containing fresh sterilising means.

11. An accessory for use with an injection device of the kind in which injectate is delivered through a hollow needle, the accessory comprising a sterilizing cap which is provided to sterilize the needle and is detachably connectable to one end of a sleeve through which the needle is moved in use, wherein the cap comprises a one piece plastic container which is adapted to be fitted to the end of the sleeve, and an annular wall which is connected to the container and is adapted to surround the end of the sleeve when the cap is fitted to the sleeve, whereby the end of the sleeve is received within the annular wall and is closed off by the cap, the container being such that the needle of the injection device may be passed therethrough and containing sterilizing means, whereby, when the cap is fitted to the sleeve, the point of the needle is sterilized by the sterilizing means as it is passed through the container.

12. An accessory as claimed in claim 11, in combination with a sleeve on which the accessory is mounted and which is disposed within said annular wall.

* * * * *

UNITED STATES PATENT AND TRADEMARK OFFICE
CERTIFICATE OF CORRECTION

PATENT NO. : 4,507,118
DATED : March 26, 1985
INVENTOR(S) : Hugh Robert DENT

It is certified that error appears in the above—identified patent and that said Letters Patent is hereby corrected as shown below:

On the title page, insert the following:

--[62]      Related U.S. Application Data

Division of Ser. No. 287,775, July 28, 1981, Patent No. 4,392,859.

[30]      Foreign Application Priority Data

July 29, 1980 [GB]  United Kingdom . . . . 8024765
       September 25, 1980 [GB]  United Kingdom . . . . 8030985
       June 2, 1981 [GB]  United Kingdom . . . . 8116830
       June 2, 1981 [GB]  United Kingdom . . . . 8116831--

Signed and Sealed this

Twenty-sixth Day of November 1985

[SEAL]

Attest:

DONALD J. QUIGG

Attesting Officer      Commissioner of Patents and Trademarks